US009269498B2

(12) United States Patent
Daley et al.

(10) Patent No.: US 9,269,498 B2
(45) Date of Patent: Feb. 23, 2016

(54) SINTERED CAPACITOR ELECTRODE INCLUDING MULTIPLE THICKNESSES

(75) Inventors: Jay E. Daley, Coon Rapids, MN (US); Mary M. Byron, Roseville, MN (US); Eric Stemen, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 853 days.

(21) Appl. No.: 12/968,561

(22) Filed: Dec. 15, 2010

(65) Prior Publication Data

US 2011/0152960 A1 Jun. 23, 2011

Related U.S. Application Data

(60) Provisional application No. 61/288,081, filed on Dec. 18, 2009.

(51) Int. Cl.
*A61N 1/05* (2006.01)
*H01G 9/06* (2006.01)
(Continued)

(52) U.S. Cl.
CPC .............. *H01G 9/06* (2013.01); *H01G 9/008* (2013.01); *H01G 9/012* (2013.01); *H01G 9/052* (2013.01); *H01G 9/08* (2013.01); *A61N 1/375* (2013.01); *A61N 1/3782* (2013.01); *Y10T 29/417* (2015.01)

(58) Field of Classification Search
CPC ..... A61N 1/39; A61N 1/3956; A61N 1/3968; H01G 2009/0412; H01G 9/02; H01G 9/04; H01G 9/042; H01G 9/048; H01G 9/052; H01G 9/08; H01G 9/145; H01G 9/155; H01G 9/06; H01G 9/008; H01G 9/012
USPC .................................................. 607/5, 9, 119
See application file for complete search history.

(56) References Cited

U.S. PATENT DOCUMENTS 3,025,441 A 3/1962 West
3,331,759 A 7/1967 Middelhoek et al.
(Continued)

FOREIGN PATENT DOCUMENTS

EP 0877400 A1 11/1998
EP 1470267 B1 4/2009
(Continued)

OTHER PUBLICATIONS

Bocek, Joseph M, et al., "Method and Apparatus for Charging Partitioned Capacitors", U.S. Appl. No. 11/462,301, filed Aug. 3, 2006, 53 pgs.
(Continued)

*Primary Examiner* — Christopher D Koharski
*Assistant Examiner* — Michael Carey
(74) *Attorney, Agent, or Firm* — Schwegman Lundberg & Woessner, P.A.

(57) ABSTRACT

An example includes a capacitor case sealed to retain electrolyte, at least one anode disposed in the capacitor case, the at least one anode comprising a sintered portion disposed on a substrate, an anode conductor coupled to the substrate in electrical communication with the sintered portion, the anode conductor sealingly extending through the capacitor case to an anode terminal disposed on the exterior of the capacitor case with the anode terminal in electrical communication with the sintered portion, a cathode disposed in the capacitor case, a separator disposed between the cathode and the anode and a cathode terminal disposed on an exterior of the capacitor case and in electrical communication with the cathode, with the anode terminal and the cathode terminal electrically isolated from one another.

10 Claims, 9 Drawing Sheets (51) Int. Cl.
*H01G 9/008* (2006.01)
*H01G 9/012* (2006.01)
*H01G 9/052* (2006.01)
*H01G 9/08* (2006.01)
*A61N 1/375* (2006.01)
*A61N 1/378* (2006.01)

(56) References Cited

U.S. PATENT DOCUMENTS

| | | |
|---|---|---|
| 3,445,731 A | 5/1969 | Saeki et al. |
| 3,627,520 A | 12/1971 | Rogers |
| 3,638,083 A | 1/1972 | Dornfeld et al. |
| 3,647,415 A | 3/1972 | Yano et al. |
| 4,059,116 A | 11/1977 | Adams |
| 4,085,397 A | 4/1978 | Yagher |
| 4,107,762 A | 8/1978 | Shirn et al. |
| 4,406,286 A | 9/1983 | Stein |
| 4,720,767 A | 1/1988 | Chan et al. |
| 4,840,122 A | 6/1989 | Nerheim |
| 4,882,115 A | 11/1989 | Schmickl |
| 5,062,025 A | 10/1991 | Verhoeven et al. |
| 5,115,378 A | 5/1992 | Tsuchiya et al. |
| RE34,879 E | 3/1995 | Bocchi et al. |
| 5,468,254 A | 11/1995 | Hahn et al. |
| 5,591,211 A | 1/1997 | Meltzer |
| 5,591,217 A | 1/1997 | Barreras |
| 5,634,938 A | 6/1997 | Swanson et al. |
| 5,660,737 A | 8/1997 | Elias et al. |
| 5,763,911 A | 6/1998 | Matthews et al. |
| 5,807,397 A | 9/1998 | Barreras |
| 5,930,109 A | 7/1999 | Fishler |
| 6,115,235 A | 9/2000 | Naito |
| 6,141,205 A | 10/2000 | Nutzman et al. |
| 6,161,040 A | 12/2000 | Blunsden |
| 6,193,779 B1 | 2/2001 | Reichert et al. |
| 6,241,751 B1 | 6/2001 | Morgan et al. |
| 6,310,757 B1 | 10/2001 | Tuzuki et al. |
| 6,347,032 B2 | 2/2002 | Naito |
| 6,350,406 B1 | 2/2002 | Satou et al. |
| 6,351,371 B1 | 2/2002 | Yoshida et al. |
| 6,385,031 B1 | 5/2002 | Lerche et al. |
| 6,456,877 B1 | 9/2002 | Fishler |
| 6,459,566 B1 | 10/2002 | Casby et al. |
| 6,493,212 B1* | 12/2002 | Clarke et al. ............ 361/521 |
| 6,509,588 B1 | 1/2003 | O'Phelan et al. |
| 6,560,089 B2 | 5/2003 | Miltich et al. |
| 6,622,046 B2* | 9/2003 | Fraley et al. ............ 607/36 |
| 6,678,559 B1 | 1/2004 | Breyen et al. |
| 6,687,118 B1 | 2/2004 | O'Phelan et al. |
| 6,699,265 B1 | 3/2004 | O'Phelan et al. |
| 6,775,127 B2 | 8/2004 | Yoshida |
| 6,778,860 B2 | 8/2004 | Ostroff et al. |
| 6,785,123 B2 | 8/2004 | Keser |
| 6,801,424 B1 | 10/2004 | Nielsen et al. |
| 6,807,048 B1 | 10/2004 | Nielsen et al. |
| 6,850,405 B1 | 2/2005 | Mileham et al. |
| 6,855,234 B2 | 2/2005 | D'Astolfo, Jr. |
| 6,865,417 B2 | 3/2005 | Rissmann et al. |
| 6,914,769 B2 | 7/2005 | Welsch et al. |
| 6,952,608 B2 | 10/2005 | Ostroff |
| 6,954,670 B2 | 10/2005 | Ostroff |
| 7,024,246 B2 | 4/2006 | Acosta et al. |
| 7,327,557 B2 | 2/2008 | Poplett |
| 7,342,774 B2 | 3/2008 | Hossick-Schott et al. |
| 7,522,957 B2 | 4/2009 | Ostroff |
| 7,531,010 B1 | 5/2009 | Feger et al. |
| 7,564,677 B2 | 7/2009 | Poplett |
| 7,760,488 B2 | 7/2010 | Breznova et al. |
| 8,179,663 B2 | 5/2012 | Brabeck et al. |
| 8,619,408 B2 | 12/2013 | Sherwood et al. |
| 8,725,252 B2 | 5/2014 | Sherwood |
| 8,873,220 B2 | 10/2014 | Sherwood et al. |
| 8,988,859 B2 | 3/2015 | Sherwood et al. |
| 9,123,470 B2 | 9/2015 | Sherwood et al. |
| 9,129,749 B2 | 9/2015 | Sherwood et al. |
| 2003/0169560 A1 | 9/2003 | Welsch et al. |
| 2004/0019268 A1 | 1/2004 | Schmidt et al. |
| 2004/0147960 A1 | 7/2004 | O'Phelan et al. |
| 2004/0147961 A1* | 7/2004 | O'Phelan et al. ............ 607/1 |
| 2004/0240155 A1 | 12/2004 | Miltich et al. |
| 2005/0017888 A1 | 1/2005 | Sherwood et al. |
| 2006/0017089 A1 | 1/2006 | Taller et al. |
| 2006/0018083 A1 | 1/2006 | Schmidt |
| 2006/0035152 A1 | 2/2006 | Nishimura et al. |
| 2006/0139580 A1 | 6/2006 | Conner et al. |
| 2006/0139850 A1* | 6/2006 | Rorvick ............ A61N 1/375 361/508 |
| 2006/0166088 A1 | 7/2006 | Hokanson et al. |
| 2006/0174463 A1 | 8/2006 | O'Phelan et al. |
| 2006/0249774 A1 | 11/2006 | Sherwood |
| 2007/0109723 A1 | 5/2007 | Kuriyama et al. |
| 2007/0188980 A1 | 8/2007 | Hossick-Schott |
| 2008/0030927 A1 | 2/2008 | Sherwood |
| 2008/0170354 A1 | 7/2008 | Dvorak et al. |
| 2008/0198534 A1 | 8/2008 | Lee et al. |
| 2008/0208270 A1 | 8/2008 | Linder et al. |
| 2009/0231782 A1 | 9/2009 | Fujita et al. |
| 2009/0237862 A1 | 9/2009 | Nielsen et al. |
| 2009/0242415 A1 | 10/2009 | Yoshimitsu |
| 2009/0273884 A1 | 11/2009 | Shimizu et al. |
| 2010/0010562 A1 | 1/2010 | Daley et al. |
| 2010/0110614 A1 | 5/2010 | Umemoto et al. |
| 2010/0110615 A1 | 5/2010 | Nishimura et al. |
| 2010/0157510 A1 | 6/2010 | Miyachi et al. |
| 2010/0193731 A1 | 8/2010 | Lee et al. |
| 2010/0195261 A1 | 8/2010 | Sweeney et al. |
| 2010/0226066 A1 | 9/2010 | Sweeney et al. |
| 2010/0226070 A1 | 9/2010 | Yang et al. |
| 2011/0038098 A1 | 2/2011 | Taira et al. |
| 2011/0149474 A1 | 6/2011 | Sherwood et al. |
| 2011/0149475 A1 | 6/2011 | Sherwood et al. |
| 2011/0152958 A1 | 6/2011 | Sherwood et al. |
| 2011/0152959 A1 | 6/2011 | Sherwood |
| 2011/0152961 A1 | 6/2011 | Sherwood |
| 2013/0141842 A1 | 6/2013 | Sherwood et al. |
| 2015/0043130 A1 | 2/2015 | Sherwood et al. |

FOREIGN PATENT DOCUMENTS

| | | |
|---|---|---|
| JP | 2003522420 A | 7/2013 |
| WO | WO-2006139850 A1 | 6/2006 |
| WO | WO-2011075506 A2 | 6/2011 |
| WO | WO-2011075506 A3 | 6/2011 |
| WO | WO-2011075508 A2 | 6/2011 |
| WO | WO-2011075508 A3 | 6/2011 |
| WO | WO-2011075511 A2 | 6/2011 |
| WO | WO-2011075511 A3 | 6/2011 |

OTHER PUBLICATIONS

"U.S. Appl. No. 12/968,523, Response filed Sep. 23, 2013 to Non Final Office Action mailed Jun. 21, 2013", 8 pgs.

"U.S. Appl. No. 12/968,523, Non Final Office Action mailed Jun. 21, 2013", 12 pgs.

"U.S. Appl. No. 12/968,523, Non Final Office Action mailed Oct. 15, 2013", 9 pgs.

"U.S. Appl. No. 12/968,523, Response filed Jan. 8, 2014 to Non-Final Office Action mailed Oct. 15, 2013", 11 pgs.

"U.S. Appl. No. 12/968,536, Response filed Sep. 23, 2013 to Non Final Office Action mailed Jun. 21, 2013", 7 pgs.

"U.S. Appl. No. 12/968,536, Non Final Office Action mailed Jun. 21, 2013", 7 pgs.

"U.S. Appl. No. 12/968,536, Non Final Office Action mailed Oct. 2, 2013", 17 pgs.

"International Application Serial No. PCT/US2010/060437, Written Opinion mailed Sep. 13, 2011", 6 pgs.

"International Application Serial No. PCT/US2010/060444, International Preliminary Report on Patentability mailed Jun. 28, 2012", 8 pgs.

"International Application Serial No. PCT/US2010/060444, International Search Report mailed Sep. 14, 2011", 4 pgs.

(56) References Cited

OTHER PUBLICATIONS

"International Application Serial No. PCT/US2011/06044, Written Opinion mailed Sep. 14, 2011", 7 pgs.
"Japanese Application Serial No. 2012-544737, Office Action mailed Nov. 5, 2013", With English Translation, 6 pgs.
"U.S. Appl. No. 12/968,523, Advisory Action mailed Sep. 22, 2014", 3 pgs.
"U.S. Appl. No. 12/968,523, Final Office Action mailed Jun. 20, 2014", 7 pgs.
"U.S. Appl. No. 12/968,523, Non Final Office Action mailed Dec. 5, 2014", 9 pgs.
"U.S. Appl. No. 12/968,523, Response filed Aug. 18, 2014 to Final Office Action mailed Jun. 20, 2014", 7 pgs.
"U.S. Appl. No. 12/968,536, Advisory Action mailed Sep. 19, 2014", 3 pgs.
"U.S. Appl. No. 12/968,536, Final Office Action mailed Jun. 19, 2014", 9 pgs.
"U.S. Appl. No. 12/968,536, Non Final Office Action mailed Jan. 16, 2015", 9 pgs.
"U.S. Appl. No. 12/968,536, Response filed Aug. 18, 2014 to Final Office Action mailed Jun. 19, 2014", 8 pgs.
"U.S. Appl. No. 12/968,571, Advisory Action mailed Jun. 3, 2014", 3 pgs.
"U.S. Appl. No. 12/968,571, Final Office Action mailed Mar. 11, 2014", 15 pgs.
"U.S. Appl. No. 12/968,571, Notice of Allowance mailed Jun. 26, 2014", 7 pgs.
"U.S. Appl. No. 12/968,571, Response filed May 12, 2014 to Final Office Action mailed Mar. 11, 2014", 9 pgs.
"U.S. Appl. No. 12/968,571, Response filed Jun. 10, 2014 to Final Office Action mailed Mar. 11, 2014", 6 pgs.
"U.S. Appl. No. 13/753,023, Non Final Office Action mailed Jul. 24, 2014", 8 pgs.
"U.S. Appl. No. 13/753,023, Notice of Allowance mailed Nov. 21, 2014", 7 pgs.
"U.S. Appl. No. 14/521,660, Preliminary Amendment filed Nov. 18, 2014", 6 pgs.
"U.S. Appl. No. 13/753,023, Response filed Oct. 22, 2014 to Non Final Office Action mailed Jul. 24, 2014", 8 pgs.
"U.S. Appl. No. 12/968,536, Response filed Jan. 2, 2014 to Non-Final Office Action mailed Oct. 2, 2013", 10 pgs.
"U.S. Appl. No. 12/968,555, Notice of Allowance mailed Apr. 2, 2013", 9 pgs.
"U.S. Appl. No. 12/968,555, Notice of Allowance mailed Aug. 28, 2013", 8 pgs.
"U.S. Appl. No. 12/968,555, Notice of Allowance mailed Nov. 23, 2012", 9 pgs.
"U.S. Appl. No. 12/968,555, Response filed Oct. 29, 2012 to Restriction Requirement mailed Sep. 27, 2012", 7 pgs.
"U.S. Appl. No. 12/968,555, Restriction Requirement mailed Sep. 27, 2012", 7 pgs.
"U.S. Appl. No. 12/968,555, Supplemental Notice of Allowability mailed Dec. 26, 2012", 2 pgs.
"U.S. Appl. No. 12/968,571, Response filed Apr. 3, 2013 to Non Final Office Action mailed Nov. 9, 2012", 13 pgs.
"U.S. Appl. No. 12/968,571, Advisory Action mailed Aug. 22, 2013", 3 pgs.
"U.S. Appl. No. 12/968,571, Final Office Action mailed Jun. 3, 2013", 14 pgs.
"U.S. Appl. No. 12/968,571, Non Final Office Action mailed Sep. 13, 2013", 15 pgs.
"U.S. Appl. No. 12/968,571, Non Final Office Action mailed Nov. 9, 2012", 15 pgs.
"U.S. Appl. No. 12/968,571, Response filed Jul. 31, 2013 to Final Office Action mailed Jun. 3, 2013", 11 pgs.
"U.S. Appl. No. 12/968,584, Response filed Oct. 29, 2013 to Non Final Office Action mailed Jul. 31, 2013", 10 pgs.
"U.S. Appl. No. 12/968,584, Non Final Office Action mailed Jan. 30, 2013", 11 pgs.
"U.S. Appl. No. 12/968,584, Non Final Office Action mailed Jul. 31, 2013", 12 pgs.
"U.S. Appl. No. 12/968,584, Notice of Allowance mailed Dec. 27, 2013", 7 pgs.
"U.S. Appl. No. 12/968,584, Response filed Apr. 26, 2013 to Non Final Office Action mailed Jan. 30, 2013", 10 pgs.
"International Application Serial No. PCT/US2010/060432, Corrected International Preliminary Report on Patentability mailed May 11, 2012", 22 pgs.
"International Application Serial No. PCT/US2010/060432, International Preliminary Report on Patentability mailed Apr. 27, 2012", 16 pgs.
"International Application Serial No. PCT/US2010/060432, Invitation to Pay Additional Fees rnailed Sep. 13, 2011", 9 pgs.
"International Application Serial No. PCT/US2010/060432, Search Report mailed Dec. 5, 2011", 6 pgs.
"International Application Serial No. PCT/US2010/060432, Written Opinion mailed Dec. 5, 2011", 14 pgs.
"International Application Serial No. PCT/US2010/060437, Search Report mailed Sep. 13, 2011", 4 pgs.
"U.S. Appl. No. 12/968,523, Notice of Allowance mailed Apr. 27, 2015", 5 pgs.
"U.S. Appl. No. 12/968,523, Response filed Mar. 6, 2015 to Non Final Office Action mailed Dec. 5, 2014", 8 pgs.
"U.S. Appl. No. 12/968,536, Notice of Allowance mailed Apr. 28, 2015", 5 pgs.
"U.S. Appl. No. 12/968,536, Response fled Apr. 16, 2015 to Non Final Office Action mailed Jan. 16, 2015", 8 pgs.
US 8,503,164, 08/2013, Sherwood et al. (withdrawn)

* cited by examiner

SINTERED CAPACITOR ELECTRODE INCLUDING MULTIPLE THICKNESSES

CROSS-REFERENCE TO RELATED APPLICATIONS

This application claims the benefit of U.S. Provisional Application No. 61/288,081, filed on Dec. 18, 2009, under 35 U.S.C. §119(e), which is incorporated herein by reference in its entirety.

TECHNICAL FIELD

This document relates generally to energy storage and particularly to sintered electrodes to store energy in an implantable medical device.

BACKGROUND

Capacitors include multiple electrodes that are interconnected to function together to charge with energy and to discharge energy. Capacitor interconnections present several challenges. Interconnections can increase equivalent series resistance, which can decrease energy density. Interconnections can also frustrate assembly, either by machine or by operator, especially if the interconnections include delicate components. Robust interconnection systems and methods that address these challenges can improve capacitors.

SUMMARY

This document discusses apparatus and methods for sintered capacitor electrodes having multiple thicknesses. One embodiment of the apparatus includes a first second and third electrode disposed in a capacitor case. Separator material separates the second electrode form the first and third electrodes. The third electrode includes a first sintered portion of a first thickness and second sintered portion of a second thickness. The second thickness of the third electrode is substantially equivalent to a thickness including the first thickness of the third electrode, the second electrode thickness, the first separator thickness and the second separator thickness. The third electrode is in electrical communication with the first electrode. One or more electrodes couple to terminals extending through the case.

An aspect of this disclosure relates to a method for making a capacitor having electrodes with varying thickness. An embodiment according to the method includes sintering material into an electrode to define a first portion having a first thickness and a second portion having a second thickness, and stacking electrodes into a stack, including stacking the electrode with additional electrodes, the stacking including abutting the second portion with a connection portion of a second electrode, with an electrically isolated electrode disposed between the electrode and the second electrode.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This application is for energy storage devices such as capacitors that include interconnections. Some of the embodiments disclosed here intersperse anodes and cathodes in a stack, with electrodes of one polarity sandwiched between two electrodes of another polarity. In such configurations, interconnecting the electrodes of a like polarity can present challenges. One challenge is that interconnecting the electrodes can damage them, such as by bending the electrodes so they are close together to connect with a third interconnection device such as a bus bar, or so that the electrodes abut. Bending the electrodes can increase equivalent series resistance and can physically damage them, such as by kinking them or even snapping them into parts.

The present application sets forth systems and methods that can reduce or eliminate the bending of electrodes. Embodiments use spacers to maintain distance between the electrodes. In some examples, the spacers are formed onto the electrodes themselves, such as by sintering. In some examples, devices such as rivets are used to space the electrodes apart.

Figure 1:
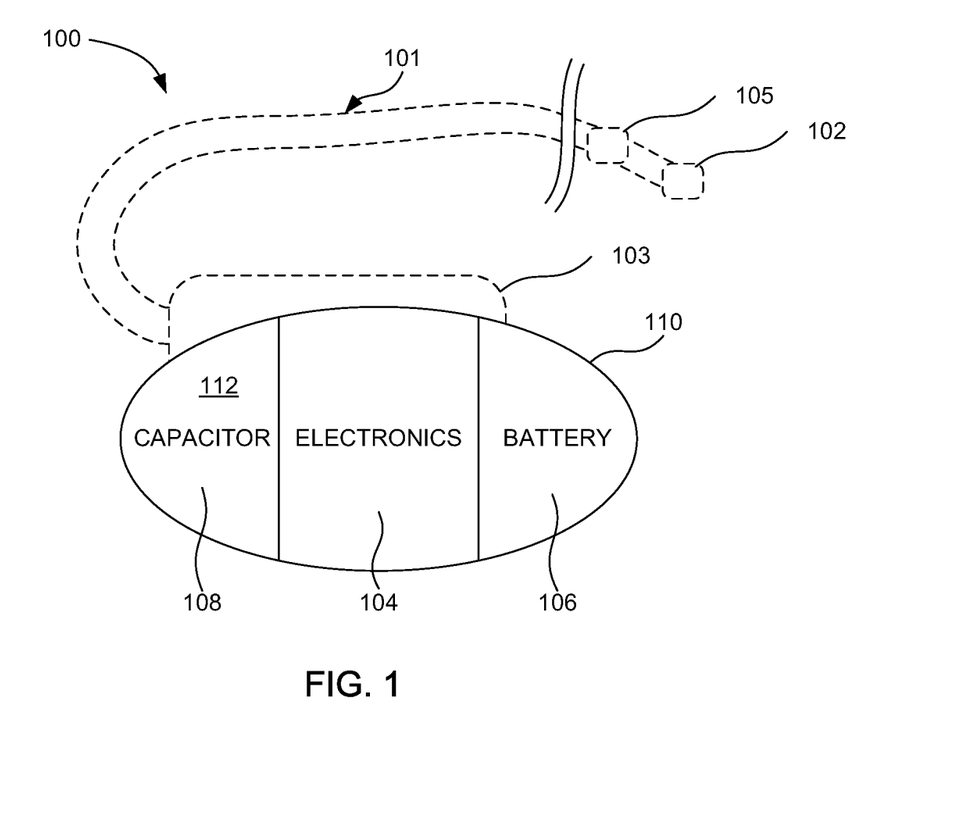
FIG. 1 is a schematic of a medical system including a sintered capacitor, according to some embodiments.

FIG. 1 is a schematic of a system 100 such as a medical system including a sintered capacitor, according to some embodiments. The system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

In various embodiments, electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. In some instances, electronics 104 are powered wirelessly using an inductor. In additional configurations, the electronics 104 are powered by a battery 106. In some examples, electronics 104 are to direct small therapeutic bursts of energy from the battery 106 to a patient.

For therapies that use energy discharge rates exceeding what battery 106 is able to provide, such as defibrillation, a capacitor 108 is used. Energy from the battery 106 is controlled by the electronics 104 to charge the capacitor 108. The capacitor 108 is controlled with the electronics 104 to discharge to a patient to treat the patient. In some examples, the capacitor 108 entirely discharges to a patient, and in additional examples is switched on to provide therapeutic energy and switched off to truncate therapy delivery.

Some examples of a system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101 and are leadless. Leadless examples are positioned in contact with the tissue to be stimulated, or are positioned proximal to a tissue to be stimulated to shock the tissue through intermediary tissue. In some examples, leadless systems are easier to implant and are less expensive as they do not use additional lead components. The housing 110 is used as an electrode in leadless configurations, in some examples.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a second electrode such as a cathode sized to deliver a defibrillation pulse of at least approximately 50 joules. This energy level is predetermined to achieve a delivered energy level mandated by a governing body or standard associated with a geographic region, such as a European country. In an additional embodiment, the anode and second electrode are sized to deliver a defibrillation pulse of at least approximately 60 joules. This energy level is predetermined to achieve an energy level mandated by a governing body of another region, such as the United States. In some examples, electronics 104 are to control discharge of a defibrillation pulse so that the medical system 100 delivers only the energy mandated by the region in which the device 100 is used.

Packaging anodes and cathodes can reduce their efficiency. Interconnections between conductors coupled to electronics and to the electrodes of the capacitor 108 decrease efficiency of charging and discharging, for example. Accordingly, anodes and cathodes are sized to compensate for decreases in efficiency. As such, in some embodiments, the capacitor 108 includes anodes and second electrodes sized and packaged to deliver a defibrillation pulse of at least approximately 50 joules. Some are sized and packaged to deliver a defibrillation pulse of at least approximately 60 joules.

One characteristic of some sintered electrode examples is that at least one anode and a cathode have a DC capacitance that is approximately 23% greater than a AC capacitance for the at least one anode and the second electrode. In some examples, the at least one anode and the second electrode have an AC capacitance of at least 96.7 microfarads per cubic centimeter at 445 total voltage. This is a 30% improvement over an etched capacitor that has 74.5 microfarads per cubic centimeter. Total voltage is the voltage that allows 1 milliamp of leakage per square centimeter. Some examples are aged to 415 volts.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form case 112, including, but not limited to, aluminum, titanium, stainless steel, nickel, a polymeric material, or combinations of these materials. The case 112 is sealed to retain electrolyte. Various electrolytes can be used including, but not limited to, Suzuki-Techno Corporation electrolyte model 1184. The case 112 includes a seal, such as a resin based seal including but not limited to epoxy, in some examples. Some examples include a rubber seal to seal case portions to one another, or to seal subcomponents such as a feedthrough to one or more case portion. In some examples, case 112 is welded together from subcomponents. Some examples include a case that includes one or more backfill ports, but the present subject matter is not so limited.

A hermetically sealed device housing 110 is used to house components, such as the battery 106, the electronics 104, and the capacitor 108. Hermeticity is provided by welding components into the hermetically sealed device housing 110 in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to any application where high-energy, high-voltage, or space-efficient capacitors are desirable, including, but not limited to capacitors used for photographic flash equipment. In other words, present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
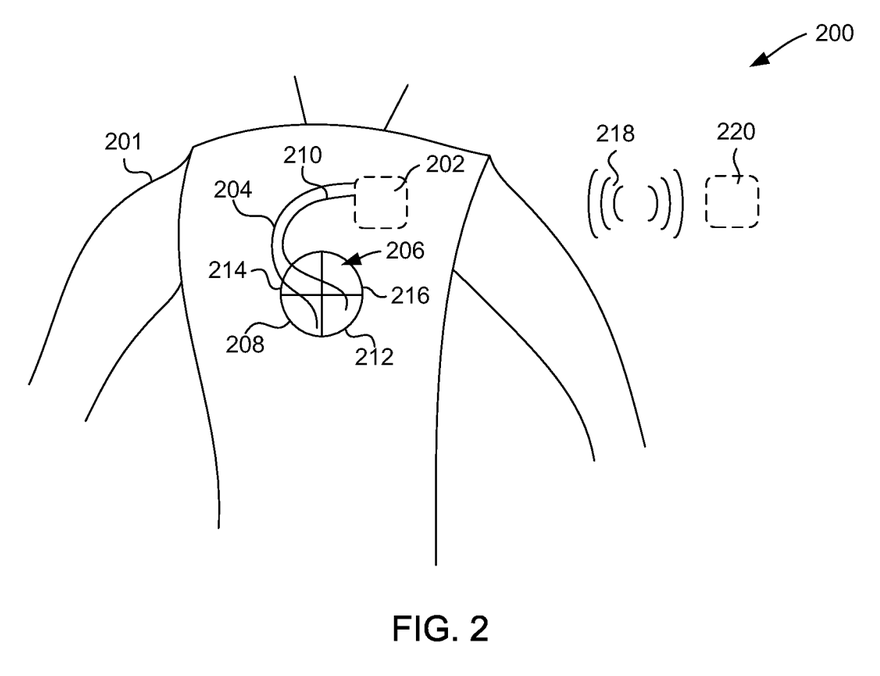
FIG. 2 is an implanted medical system including a sintered capacitor, according to some embodiments.

FIG. 2 is an implanted medical system 200, implanted in a patient 201, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both those tissue regions. The second lead 210 is in direct contact with the right atrium 216 and the right ventricle 212 to sense and/or stimulate both of those tissue regions. The cardiac rhythm management device 202 uses the lead electrodes to deliver energy to the heart, between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202. Other stimulation topologies, such as those that stimulate other portions of the body, additionally benefit from the apparatus, systems and methods disclosed herein.

Figure 3A:
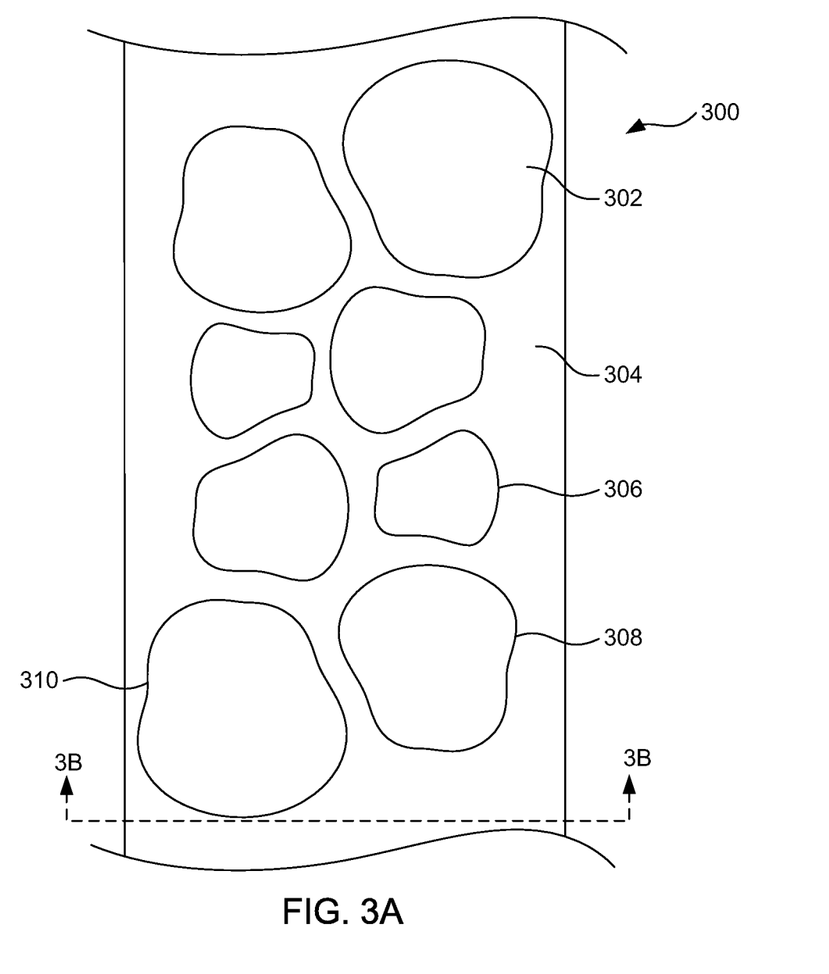
FIG. 3A is a plan view of nested sintered capacitor electrodes that have yet to be excised from a substrate, according to some embodiments.
Figure 3B:
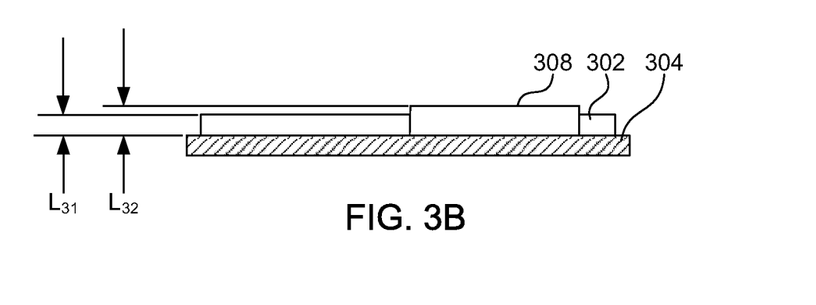
FIG. 3B is a cross section taken along the line 3B-3B in FIG. 3A.

FIG. 3A is a plan view of nested sintered capacitor electrodes that have yet to be excised from a substrate, according to some embodiments. FIG. 3B is a cross section taken along the line 3B-3B in FIG. 3A. Electrodes 302 are sintered onto a substrate 304. A first sintered portion 310 has a thickness of $L_{31}$. In various embodiments, a second sintered portion 308 has a thickness $L_{32}$. In certain examples, the thickness $L_{32}$ is greater than the thickness $L_{31}$.

In some examples, the web 300 is used in constructing a capacitor. In additional examples, sintered portions are excised from the web 300 for use in constructing a capacitor. In some examples, an electrode is cut from the web 300 on the illustrated perimeters such as perimeter 306. In some of these examples, the sintered material is not excised. In additional examples, the sintered material is brushed or smeared by an excision device. In additional examples, an electrode is cut from the web 300 by cutting around and outside the web 300. In these embodiments, foil extends beyond a perimeter of the sintered material. Foil that extends beyond a perimeter of sintered material is used in constructing a capacitor in some examples, such as by interconnecting multiple electrodes by interconnecting their respective foils. Examples of foils used for interconnection are disclosed herein. In various examples, an electrode is cut from the web 300 by cutting inside the perimeter 306, such that sintered material is cut.

In some embodiments, the first portion 310 and the second portion 308 are formed with the same sintering process. In additional examples, separate sintering processes are used. In various examples, one or both of the first portion 310 and the second portion 308 are formed by one or more processes including, but not limited to, sintering, selective laser sintering, direct metal laser sintering, doping a material with a conductive dopant, forming a portion of a conductive adhesive such as a conductive epoxy and melting a dopant. In some examples, the thickness of one or both of the first portion 310 and the second portion 308 is defined using a mechanical process such as planeing, grinding, sanding or another process. The thickness of the first portion and the second portion are controlled within specified manufacturing tolerances so that a stack of electrodes can additionally fall within a specified tolerance. A stack of electrodes having different widths between respective first portions and second portions allows for a side profile of the stack to have a contour defined by varying first portions, while the stack defined by the second portions has a rectangular cross section.

Figure 4A:
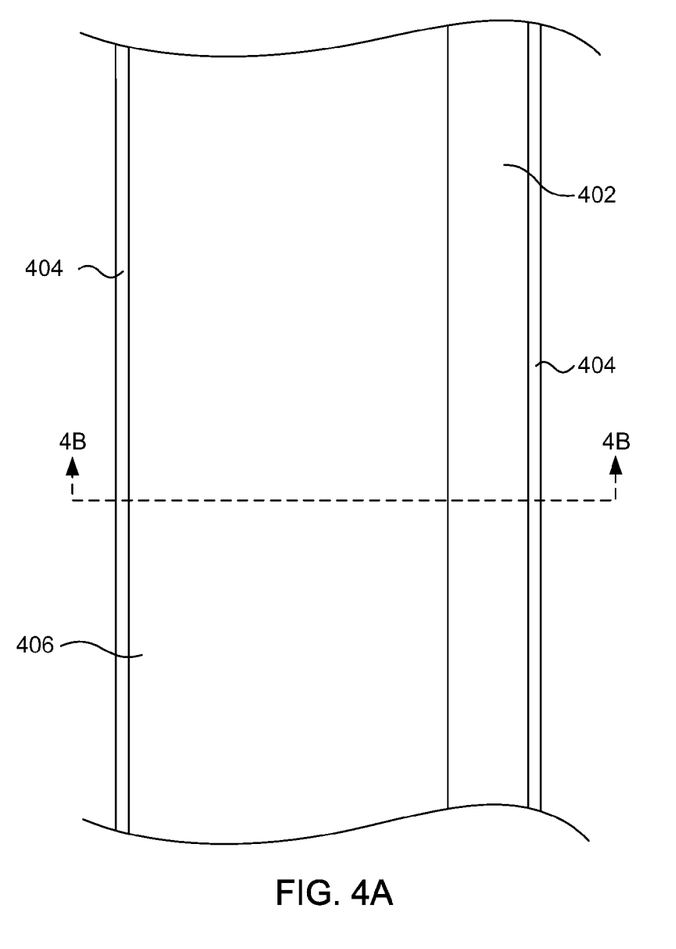
FIG. 4A is a plan view of a web, according to some embodiments.
Figure 4B:
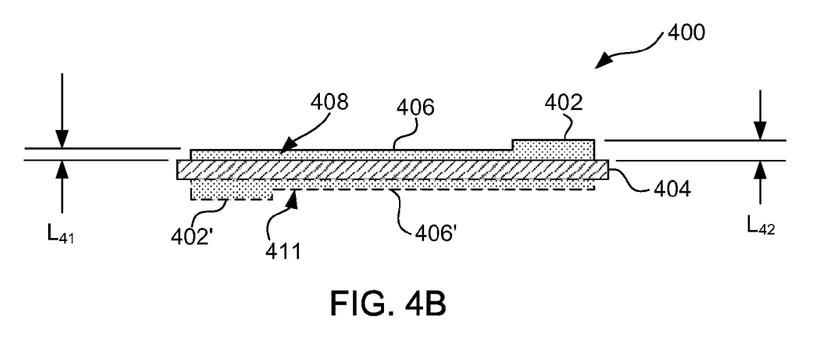
FIG. 4B is a cross section taken along the line 4B-4B in FIG. 4A.

FIG. 4A is a plan view of a web, according to some embodiments. FIG. 4B is a cross section taken along the line 4B-4B in FIG. 4A. The web includes material 408 disposed on a substrate 404. The substrate 404 is formed of a metallic foil in various examples. In some examples, the substrate 404 is an aluminum foil. The substrate 404 has a thickness of less than 0.008 inches (0.2 mm) in various examples. Some aluminum foils are less than or equal to 0.005 inches thick. These foils are easily bent by hand and are easily torn by hand. Substrates that are thicker are additionally possible. Examples of substrate materials include aluminum, titanium, copper, nickel and alloys thereof. In some examples, the web 400 is feedable through a reel-to-reel process.

In certain examples the material 408 is sintered onto the substrate. In various examples, one or both of the first portion 406 and the second portion 402 are formed by one or more processes including, but not limited to, sintering, selective laser sintering, direct metal laser sintering, doping a material with a conductive dopant, forming a portion of a conductive adhesive such as a conductive epoxy and melting a dopant. In some examples, the material is sintered to define a first portion 406 and a second portion 402. The first portion 406 has a thickness $L_{41}$, and the second portion 402 has a thickness $L_{42}$. In some embodiments these thicknesses are equivalent or substantially equivalent (e.g., within a selected manufacturing tolerance). Some embodiments include a first portion 406 having a thickness that is less than the second thickness 402. Optionally, the web 400 includes sintered material 408 on a first side of the substrate 406 and a second sintered material 411 on a second side of the substrate 406. In some embodiments, the second sintered material 411 includes portions with different thicknesses 406', 402'. In some embodiments the thickness of the portions 406', 402' are equivalent or substantially equivalent (e.g., within a selected manufacturing tolerance). It is understood that in embodiments described herein showing an electrode including a substrate with a sintered portion on one side of the substrate, that it is possible to have instead, an electrode including a substrate with sintered material on two sides of the substrate without departing from the scope of the present subject matter.

In some examples the first portion 406 and the second portion 402 are continuous and monolithic—a state defined by the sintered material being sintered in a single sintering step such that the metal grains of the first portion 406 and the second portion 402 appear uniform when viewed across a boundary between the first portion 406 and the second portion 402.

In some embodiments, the first portion 406 and the second portion 402 are formed with the same sintering process. In additional examples, separate sintering processes are used. In various examples, one or both of the first portion 406 and the second portion 402 are formed by one or more processes including, but not limited to, sintering, selective laser sintering, direct metal laser sintering, doping a material with a conductive dopant, forming a portion of a conductive adhesive such as a conductive epoxy and melting a dopant. In some examples, the thickness of one or both of the first portion 406 and the second portion 402 is defined using a mechanical process such as planeing, grinding, sanding or another process. The thickness of the first portion and the second portion are controlled within specified manufacturing tolerances so that a stack of electrodes can additionally fall within a specified tolerance. A stack of electrodes having different widths between respective first portions and second portions allows for a side profile of the stack to have a contour defined by varying first portions, while the stack defined by the second portions has a rectangular cross section.

Figure 5A:
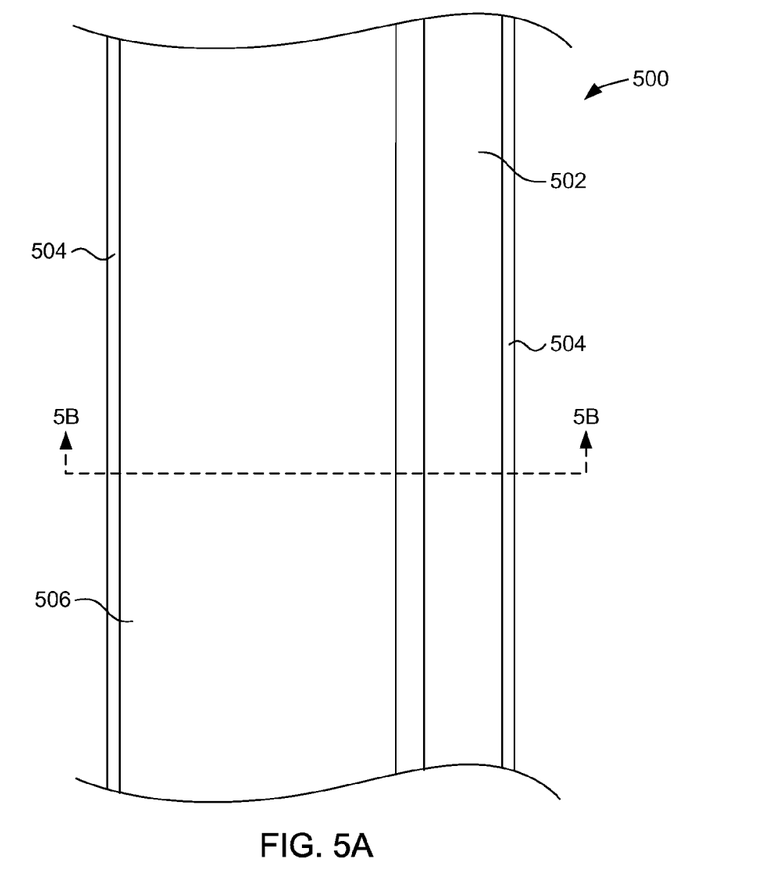
FIG. 5A is a plan view of one or more sintered capacitor electrodes including multiple thicknesses, according to some embodiments.
Figure 5B:
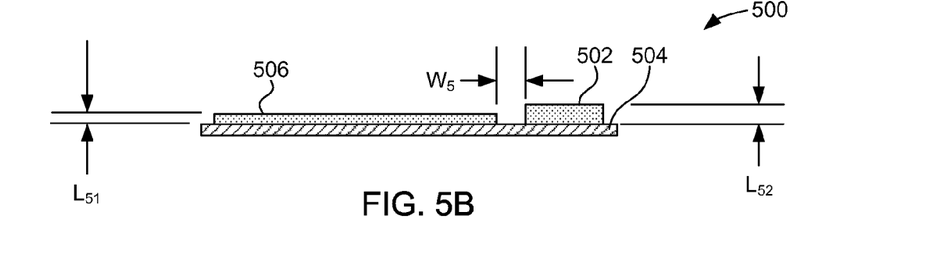
FIG. 5B is a cross section taken along the line 5B-5B in FIG. 5A.

FIG. 5A is a plan view of one or more sintered capacitor electrodes including multiple thicknesses, according to some embodiments. FIG. 5B is a cross section taken along the line 5B-5B in FIG. 5A. The web includes material disposed on a substrate 504. The substrate 504 is formed of a metallic foil in various examples. In some examples, the substrate 504 is an aluminum foil. The substrate 504 has a thickness of less than 0.008 inches (0.2 mm) in various examples. Some aluminum foils are less than or equal to 0.005 inches thick. These foils are easily bent by hand and are easily torn by hand. Substrates that are thicker are additionally possible. Examples of substrate materials include aluminum, titanium, copper, nickel and alloys thereof. In some examples, the web 500 is feedable through a reel-to-reel process.

Certain examples include a material sintered onto the substrate. In certain examples, the material is sintered to define a first portion 506 and a second portion 502. The first portion has a thickness $L_{51}$, and the second portion has a thickness $L_{52}$. In some embodiments these thicknesses are equivalent or substantially equivalent (e.g., within a selected manufacturing tolerance). Some embodiments include a first portion having a thickness that is less than the second thickness.

In some embodiments, the first portion 506 and the second portion 502 are formed with the same sintering process. In additional examples, separate sintering processes are used. In various examples, one or both of the first portion 506 and the second portion 502 are formed by one or more processes including, but not limited to, sintering, selective laser sintering, direct metal laser sintering, doping a material with a conductive dopant, forming a portion of a conductive adhesive such as a conductive epoxy and melting a dopant. In some examples, the thickness of one or both of the first portion 506 and the second portion 502 is defined using a mechanical process such as planeing, grinding, sanding or another process. The thickness of the first portion and the second portion are controlled within specified manufacturing tolerances so that a stack of electrodes 500 can additionally fall within a specified tolerance. A stack of electrodes having different widths between respective first portions and second portions allows for a side profile of the stack to have a contour defined by varying first portions, while the stack defined by the second portions has a rectangular cross section.

Figure 6A:
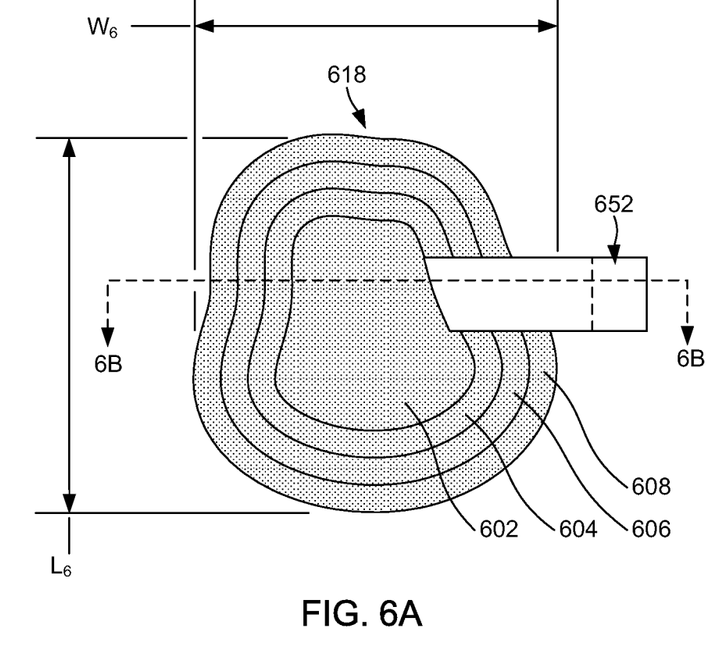
FIG. 6A is a plan view of one or more sintered capacitor electrodes including multiple thicknesses, according to some embodiments.
Figure 6B:
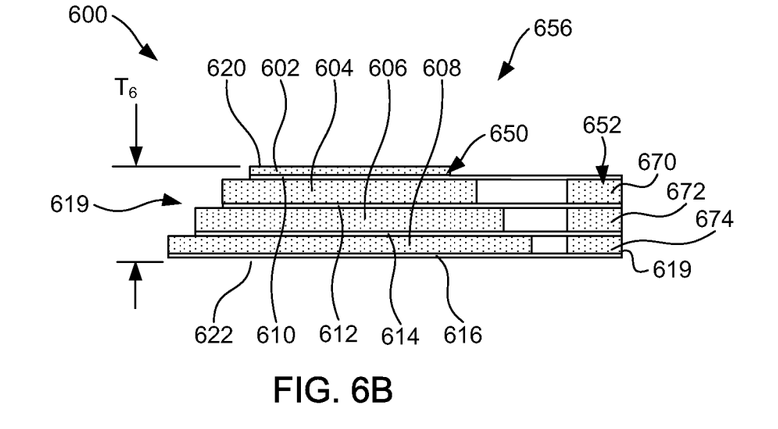
FIG. 6B is a cross section taken along the line 6B-6B in FIG. 6A.

FIG. 6A is a plan view of a capacitor stack, according to some embodiments. FIG. 6B is a front view of the capacitor stack of FIG. 6A, illustrating interconnects, according to some embodiments. In some embodiments, the stack 600 is an anode. To increase surface area of an electrode, several electrodes are positioned against one another. In certain examples, each electrode includes one or more sintered portions disposed on a substrate. A first electrode includes a main portion 602 and a substrate 610. A second electrode includes a second main portion 604 and a second substrate 612, with a second connection portion 670 additionally disposed on the substrate 612. A third electrode includes a third sintered portion 606 and a third substrate 614, with a third connection portion 672 additionally disposed on the third substrate 614. A fourth electrode includes a fourth sintered portion 608 and a fourth substrate 616, with a fourth connection portion 674 additionally disposed on the substrate 616. The present subject matter is not limited to stacks of sintered material and extends to stacks of other materials, such as etched material.

In various examples, the electrodes are interconnected to one another physically and electrically. A stack of first portions 650 defines a contoured side profile 619 in some examples. In certain embodiments, a stack of second portions 652 has a rectangular cross section. Embodiments in which both the first stack and the second stack have a rectangular cross section are possible. Additionally, some examples define a contoured side profile of each of a stack of first portions and a stack of second portions.

In some examples, one or more of the second portions 652 include additional material to melt during a welding procedure to interconnect multiple electrodes. For example, connection portion 670 includes weld filler material in some embodiments, the weld filler material to melt and interconnect the substrate 610 to the substrate 612.

In some examples, the electrodes each abut one another and are electrically connected via the abutment. In some examples, the sintered portions are welded to one another using resistance welding, such as by applying a voltage across several electrodes along the axis of stacking. In some examples, several electrodes are interconnected by interconnecting their respective substrates such as by adhesion, welding, fasteners, or combinations thereof. In some examples, substrates are interconnected to define a side profile 619 such as an edge face. Along the side profile 619, interconnection configurations include, but are not limited to, welding (including, but not limited to, laser welding), adhesion fasteners, and combinations thereof. Additionally, the substrates can be resistance welded together such as by pinching and welding.

In the illustrated configuration, a first sintered portion 602 is sintered onto a first substrate 610, and a second sintered portion 604 is sintered onto a second substrate 612. The first substrate 610 faces the second sintered portion 604 and abuts it. In additional configurations, the second electrode is flipped, and the first substrate 610 abuts the second substrate 612.

In the illustrated configuration, the plurality of anodes are stacked to a stack height $T_6$, and at least two of the sintered anodes have respective widths, perpendicular to the height $T_6$, that are substantially different such that the plurality of sintered anodes define a contoured edge 618, with the contoured edge 618 extending between a top major face 620 of a top sintered portion 602 and a bottom major face 622 of a bottom substrate 616. Various examples have an overall width $W_6$ perpendicular to the height $T_6$. In some examples at least two of the sintered anodes have respective lengths, perpendicular to the height $T_6$, that are substantially different such that the plurality of sintered anodes define a side profile 619, such as a contoured edge, with the side profile 619 extending between a top major face 620 of a top sintered portion 602 and a bottom major face 622 of a bottom substrate 616. Accordingly, the top major face 620 and the bottom major face 622 have different areas. The top major face 620 and the bottom major face 622 are substantially parallel. Various embodiments have an overall length $L_6$.

In another configuration, the plurality of electrodes are stacked to a stack height $T_6$, and at least two of the sintered anodes have respective widths, perpendicular to the height $T_6$, that are substantially equal such that the plurality of sintered anodes define a side surface that is substantially parallel to the height $T_6$. In the illustrated configuration, the top major face 620 and the bottom major face 622 are shaped similarly, but in additional embodiments, they are shaped differently.

Figure 7A:
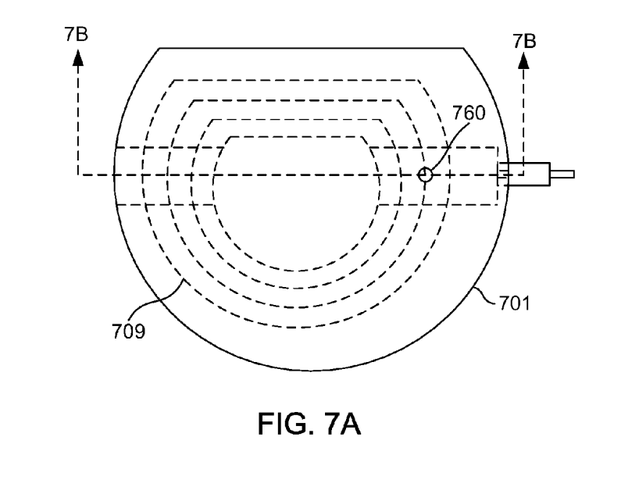
FIG. 7A is a top view of a capacitor stack, according to some embodiments.
Figure 7B:
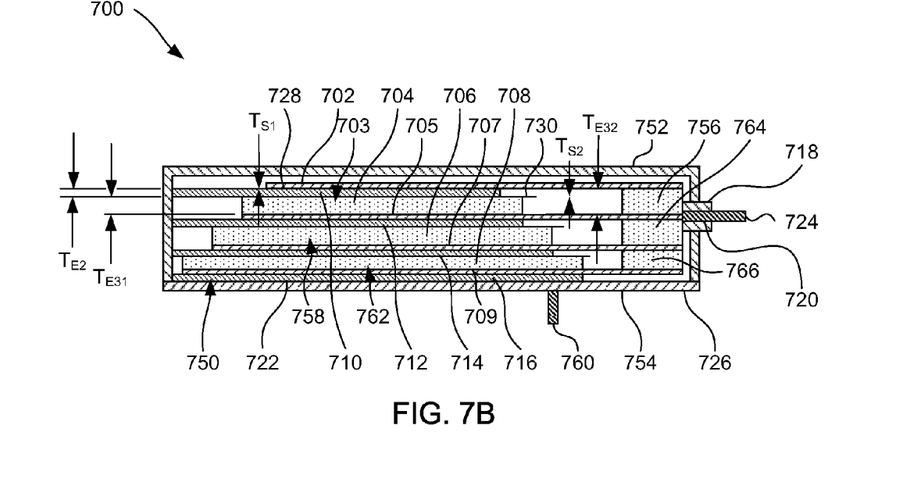
FIG. 7B is a cross section taken along the line 7B-7B in FIG. 7A.

FIG. 7A is a top view of a capacitor stack, according to some embodiments. FIG. 7B is a cross section taken along the line 7B-7B in FIG. 7A. In various embodiments, a stack 750 is disposed in a capacitor case 701. In some examples, the case 701 is sealed to retain electrolyte. Examples of seals include welds, gasketed seals such as those using o-rings, adhesives and other seals. In some examples the case 701 includes a dish portion 752 and lid portion 754.

Various embodiments include a first electrode 702 disposed in the stack 750. In certain examples, a conductor 720 is coupled to the first electrode 702, with the first electrode 702 in electrical communication with the conductor 720. In some examples, the conductor 720 sealingly extends through the capacitor case 701. In some examples, the conductor 720 forms a terminal 724 disposed on an exterior 726 of the capacitor case 701, the terminal 724 to be coupled to a wire harness or other circuitry. In additional embodiments, the conductor 720 couples to a terminal to be connected to another wire harness or other circuitry. In various embodiments, the terminal 724 is in electrical communication with the first electrode 702.

Various embodiments include a second electrode 710 that has a second electrode thickness $T_{E2}$. The second electrode 710 is in the stack 750 in some examples. In various embodiments, the second electrode 710 is disposed in the stack 750 with the first electrode 702. In various embodiments, the second electrode 710 is sealed into the case 701.

The stack 750 in some examples includes a third electrode 703 that includes a first sintered portion 704, and a substrate 705. In some examples, the stack 750 includes a fourth electrode includes a sintered portion 706 and a substrate 707. Some examples include a fifth electrode that includes a sintered portion 708 and a substrate 709. The present subject matter is not limited to stacks of sintered material and extends to stacks of other materials, such as etched material.

In various embodiments, a first separator 728 is disposed between the first electrode 702 and the second electrode 710. The separator 728 has a first separator thickness $T_{S1}$. Separator contemplated includes Kraft paper. Some examples include one or more electrodes of 0.0005 inch thick Kraft paper, although the present subject matter is not so limited and other separators are used in additional embodiments.

In some examples, a third electrode 703 is in electrical communication with the first electrode 702. In various embodiments, the third electrode 703 has a first sintered portion 704 of a first thickness $T_{E31}$. A second portion 756 of the third electrode 703 has a second thickness of $T_{E32}$. In some examples, the thickness $T_{E32}$ is a thickness other than the first thickness $T_{E31}$. Various embodiments include a second separator 730 disposed between the third electrode 703 and the second electrode 710 having a second separator thickness $T_{S2}$. In some examples, one or more of the portion 756 include filler material to fill space between the substrates that sandwich them, such as by melting during a welding operation to interconnect several electrodes.

Various embodiments include a second terminal 760 disposed on the exterior 726 of the capacitor case 701. In some examples, the second terminal 760 is in electrical communication with the second electrode 710, with the terminal 724 and the second terminal 760 electrically isolated from one another. In various embodiments, the second thickness $T_{E32}$ of the third electrode 703 is substantially the same as a thickness including the first thickness $T_{E31}$ of the third electrode 703, the second electrode thickness $T_{E2}$, the first separator thickness $T_{S1}$ and the second separator thickness $T_{S2}$.

Some examples include a plurality of electrodes stacked together touching one another, such as by abutting one another physically. In some of these examples, the electrodes are anodes. Some of these examples are configured such that each of the plurality of electrodes includes a sintered portion disposed on a respective substrate. For example, the third electrode 703 includes a first sintered portion 704 and a second sintered portion 756, each disposed on a substrate 705.

In some examples, electrodes of a plurality of electrodes are electrically interconnected to one another. For example, electrodes 703, 758 and 762 are stacked together in electrical communication with one another. In various embodiments, portions of these electrodes abut and are in electrical communication with one another. For example, portions 756, 764 and 766 abut and are in electrical communication with one another. In some examples, a stack of electrodes is constructed in which a first electrode 702 abuts a third electrode 703. In some of these examples, the first electrode 702 abuts a sintered portion 756 of the second electrode 703. In some examples, the third electrode 703 includes a substrate 705 that abuts a sintered portion 764 of electrode 758. In some examples, electrode 758 includes a substrate 707 that abuts a sintered portion 766 of a third electrode 762.

Figure 8A:
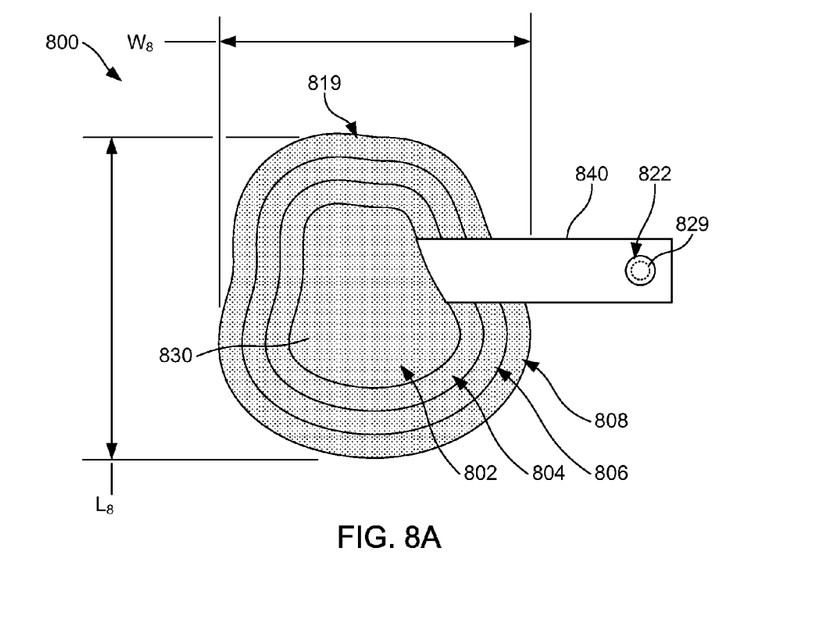
FIG. 8A is a top view of an electrode stack including rivets, according to some embodiments.
Figure 8B:
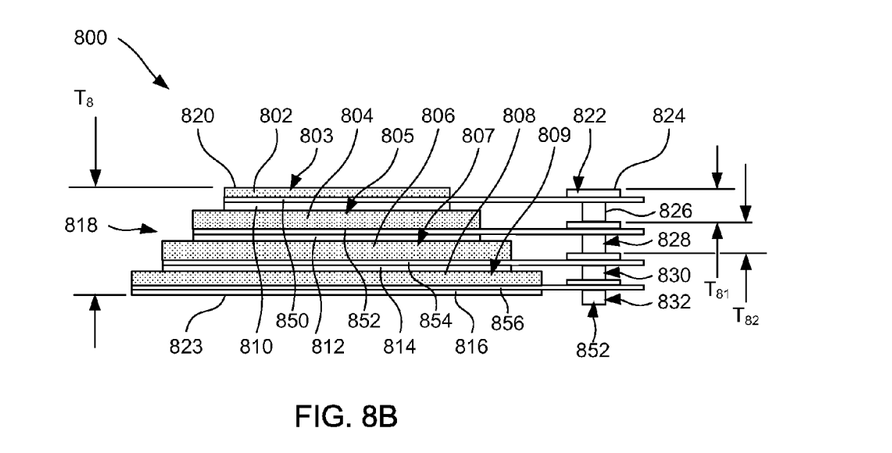
FIG. 8B is a front view of the electrode stack of FIG. 8A, illustrating rivets of different thicknesses, according to some embodiments.

FIG. 8A is a top view of an electrode stack including rivets, according to some embodiments. FIG. 8B is a front view of the electrode stack of FIG. 8A, illustrating rivets of different thicknesses, according to some embodiments. In some embodiments, the stack 800 forms part of a capacitor.

In various embodiments, the stack 800 includes a first electrode 803, a second electrode 805, a third electrode 807 and a fourth electrode 809. In some examples, each of these electrodes includes a respective sintered material disposed on a substrate. For example, the first electrode 803 includes a first sintered material 802 disposed on a first substrate 850. In certain examples, the second electrode 805 includes a second sintered material 804 disposed on a second substrate 852. In various examples, the third electrode 807 includes a third sintered material 806 disposed on a third substrate 854. In some examples, the fourth electrode 809 includes a fourth sintered material 808 disposed on a fourth substrate 856.

In various embodiments, each of the electrodes includes a connection member. For example, the first electrode 803 includes a first connection member 840. In various embodiments, the first connection member 840 defines an aperture 829. In various embodiments, the aperture is an excised portion created by any of a laser, punch, drill or combinations thereof. In various embodiments, disposed in the aperture 829 is a rivet 822. In some examples, the second electrode is coupled with a second rivet 828. In some examples, the third electrode is coupled with a third rivet 830. In some examples, the fourth electrode is coupled with a fourth rivet 832. In various examples, the first rivet 822 has a first thickness $T_{81}$. In some examples, the second rivet 828 has a second thickness $T_{82}$. In various embodiments, the first thickness $T_{81}$ is different than the second thickness $T_{82}$, however embodiments in which they are the same or similar (e.g., within a predetermined manufacturing tolerance) form part of the present subject matter.

In various embodiments, the electrodes physically contact one another via their respective rivet. The rivets are stacked into a rivet stack 852. In some examples, the thickness of one or more rivets is defined by an excision such as a grinding process. Other excision processes are possible. The present subject matter is not limited to stacks of sintered material and extends to stacks of other materials, such as etched material.

In various examples, the rivets are interconnected to one another mechanically and electrically. In some examples, the rivets each abut one another and are electrically connected via the abutment. In some examples, the rivets are welded to one another using resistance welding, such as by applying a voltage across several rivets, such as along the axis of stacking.

In the illustrated configuration, the plurality of anodes are stacked to a stack height $T_8$, and at least two of the electrodes have respective widths, perpendicular to the height $T_8$, that are substantially different such that the plurality of sintered anodes define a contoured edge 818, with the contoured edge 818 extending between a top major face 820 of a top sintered material 802 and a bottom major face 823 of a bottom substrate 816. In various embodiments, the stack 800 has an overall width $W_8$. In some examples at least two of the sintered anodes have respective lengths, perpendicular to the height $T_8$, that are substantially different such that the plurality of sintered anodes define a contoured edge 819, with the contoured edge 819 extending between a top major face 820 of a top sintered material 802 and a bottom major face 823 of a bottom substrate 816. In various embodiments, the stack 800 has an overall length $L_8$. Accordingly, the top major face 820 and the bottom major face 823 have different areas. The top major face 820 and the bottom major face 823 are substantially parallel.

In another configuration, the plurality of slugs are stacked to a stack height $T_8$, and at least two of the sintered anodes have respective widths, perpendicular to the height, that are substantially equal such that the plurality of sintered anodes define a side surface that is substantially parallel to the height $T_8$. In the illustrated configuration, the top major face 820 and the bottom major face 823 are shaped similarly, but in additional embodiments, they are shaped differently.

Figure 9:
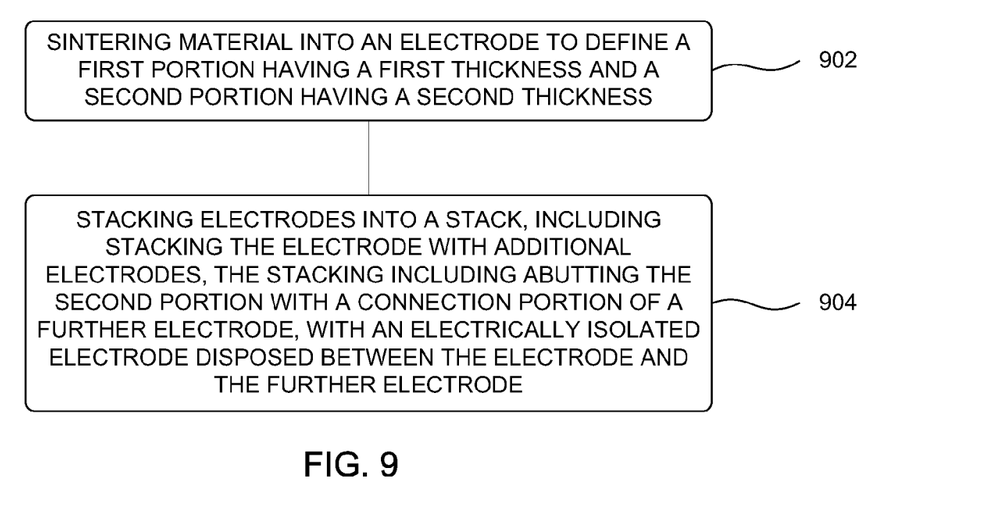
FIG. 9 is a method of making a capacitor including electrodes having different thicknesses, according to some embodiments.

FIG. 9 is a method of making a capacitor including electrodes having different thicknesses, according to some embodiments. At 902, an example method includes sintering material into an electrode to define a first portion having a first thickness and a second portion having a second thickness. At 904, an example method includes stacking electrodes into a stack, including stacking the electrode with additional electrodes, the stacking including abutting the second portion with a connection portion of a second electrode, with an electrically isolated electrode disposed between the electrode and the second electrode. Methods are contemplated in which stacking the electrodes includes maintaining the electrode in a planar shape. In certain methods, stacking the electrodes includes maintaining the second electrode in a planar shape. In some methods, stacking includes disposing separator between the electrode and the second electrode. Some methods include etching the second electrode. In some methods sintering material into an electrode includes sintering material onto a substrate. Some methods include riveting a rivet through the substrate to at least partially define the second thickness. Additional methods include sintering material into an electrode includes sintering material onto a web, with one side of the web defining the first thickness and the second portion defining the second thickness. Some methods include excising the electrode from the web. Additional methods include forming the second portion of a conductive epoxy. Some methods include forming the second portion by sintering material and doping the sintered material with a conductive epoxy. Some methods include melting a sintered material into the second portion. Some methods include melting a dopant into the second portion. Some methods include selective laser sintering a material into the second portion. Some methods include direct metal laser sintering a material into the second portion.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
  a capacitor case sealed to retain electrolyte;
  a first electrode disposed in the capacitor case;
  a conductor coupled to the first electrode in electrical communication with the conductor, the conductor sealingly extending through the capacitor case to a terminal disposed on an exterior of the capacitor case, with the terminal in electrical communication with the first electrode;
  a second electrode disposed in the capacitor case in a stack with the first electrode and adjacent the first electrode, the second electrode having a second electrode thickness;
  a first separator disposed between the first electrode and the second electrode and having a first separator thickness;
  a third electrode disposed in the capacitor in the stack with the first electrode and the second electrode and adjacent the second electrode, the third electrode in electrical communication with the first electrode and including a first sintered portion of a first thickness, and a second portion of a second thickness larger than the first thickness;
  a second separator disposed between the third electrode and the second electrode and having a second separator thickness; and
  a second terminal disposed on the exterior of the capacitor case and in electrical communication with the second electrode, with the terminal and the second terminal electrically isolated from one another,
  wherein the second thickness of the third electrode is substantially equivalent to a total thickness of the first thickness of the third electrode plus the second electrode thickness plus the first separator thickness plus the second separator thickness.

2. The apparatus of claim 1, wherein a plurality of anodes, each including a sintered portion disposed on a respective substrate of a plurality of substrates, are stacked against one another and electrically interconnected to one another.

3. The apparatus of claim 1, wherein the second portion includes a sintered portion.

4. The apparatus of claim 3, wherein the sintered portion is disposed on a substrate that extends between the first sintered portion and the second portion, with the first sintered portion and the second portion separated by a space.

5. The apparatus of claim 1, wherein the second portion includes a conductive epoxy.

6. The apparatus of claim 5, wherein the second portion includes a sintered portion doped with the conductive epoxy.

7. A system, comprising:
  a hermetically sealed device housing;
  a battery disposed in the hermetically sealed device housing;
  a capacitor disposed in the hermetically sealed device housing, the capacitor comprising:
  a capacitor case sealed to retain electrolyte;
  a first electrode disposed in the capacitor case;
  a conductor coupled to the first electrode in electrical communication with the conductor, the conductor sealingly extending through the capacitor case to a terminal disposed on an exterior of the capacitor case, with the terminal in electrical communication with the first electrode;

a second electrode disposed in the capacitor case in a stack with the first electrode and adjacent the first electrode, the second electrode having a second electrode thickness;

a first separator disposed between the first electrode and the second electrode and having a first separator thickness;

a third electrode disposed in the capacitor in the stack with the first electrode and the second electrode and adjacent the second electrode, the third electrode in electrical communication with the first electrode and including a first sintered portion of a first thickness, and a second portion of a second thickness larger than the first thickness;

a second separator disposed between the third electrode and the second electrode and having a second separator thickness; and a second terminal disposed on the exterior of the capacitor case and in electrical communication with the second electrode, with the terminal and the second terminal electrically isolated from one another, wherein the second thickness of the third electrode is substantially equivalent to a total thickness of the first thickness of the third electrode plus the second electrode thickness plus the first separator thickness plus the second separator thickness, and an electronic cardiac rhythm management circuit coupled to the battery and the capacitor and adapted to discharge the capacitor to provide a therapeutic defibrillation pulse.

8. The system of claim 7, wherein the electronic cardiac rhythm management circuit comprises a defibrillator circuit.

9. The system of claim 8, wherein first electrode is part of an anode and the second electrode is part of a cathode, and the defibrillator circuit is to discharge the anode and the cathode to provide a single therapeutically effective defibrillator pulse.

10. The system of claim 9, wherein the anode and the cathode are sized and packaged to deliver a defibrillation pulse of approximately 50 joules.

* * * * *